United States Patent [19]

LeVeen et al.

[11] Patent Number: 4,837,017

[45] Date of Patent: Jun. 6, 1989

[54] UREASE ANTIGEN PRODUCT AND PROCESS

[76] Inventors: Harry H. LeVeen; Robert F. LeVeen, both of 321 Confederate Cir., Charleston, S.C. 29407; Eric G. LeVeen, 141 South Battery, Charleston, S.C. 29401

[21] Appl. No.: 25,073

[22] Filed: Mar. 12, 1987

[51] Int. Cl.$^4$ .............................................. A61K 39/00
[52] U.S. Cl. ........................................ 424/88; 424/92; 530/403
[58] Field of Search .................... 530/403; 424/88, 92

[56] References Cited

U.S. PATENT DOCUMENTS

| | | | |
|---|---|---|---|
| 3,876,504 | 4/1975 | Koffler | 195/103.5 R |
| 4,004,979 | 1/1977 | Avrameas et al. | 195/68 |
| 4,246,351 | 1/1981 | Miyake et al. | 435/182 |
| 4,464,468 | 8/1984 | Avrameas et al. | 435/177 |

OTHER PUBLICATIONS

Hedelin et al., "Urease-Induced Crystallization In Synthetic Urine", J. of Urol., vol. 133, 529–532.

Stalheim et al., "Ureaplasmal Epithelial Lesions Related to Ammonia", Infec. & Imm., 3/1977; 15(3); 995–6.

Primary Examiner—Morton Foelak
Assistant Examiner—Samuel A. Acquah
Attorney, Agent, or Firm—Gipple & Hale

[57] ABSTRACT

The present invention relates to a non-enzymatic and non-toxic urease antigen and a method for its production. Administration of the urease antigen in living organisms serves to immunize the same from certain types of ammonia production without causing ammonia toxicity when injected, thereby promoting several advantageous biological activities including the promotion of wound healing, and general immunity from ammonia toxicity and the related effects thereof, and the cessation of toxic ammonia production in infections caused by urea splitting organisms.

17 Claims, No Drawings

UREASE ANTIGEN PRODUCT AND PROCESS

BACKGROUND OF THE INVENTION

The present invention relates to a composition, and method for production of an enzymatically inactive urease antigen and the use thereof for urease immunization which leads to the prevention of ammonia toxicity in humans. More specifically, the present invention sets forth a method of production and use of a non-enzymatic and non-toxic urease antigen which serves to immunize humans and animals thus protecting them from the harmful effects of ammonia production by urea splitting bacteria.

Ammonia and ammonia containing molecules are exceedingly toxic for the living organisms. The synthesis of nucleic acids, which are the building blocks of DNA and RNA, and which carry genetic information from generation to generation is impaired by ammonia. (AM J Physiol 223:1004, 1972).

While nitrogen containing compounds are crucial to life, free ammonia is extremely toxic to living organisms. The precise mechanism by which ammonia exerts these toxic effects is imperfectly understood. Various studies have shown that even small increases in the concentration of ammonia in living organisms lead to a decrease in the life span of cells. (Fed. Proc 31:1178, 1972). Specifically, elevated ammonia concentrations have been shown to reduce the life span of both white and red blood cells in human blood, and blood cell counts drop after urease or ammonia injection. Further, even cells that survive a higher concentration of ammonia are functionally impaired and are often permanently injured. It is believed that ammonia exerts its acute toxicity by interfering with enzyme reactions, causing swelling of mitochondria and rhexis of the nucleus. (Proc Soc Exp Biol Med 139:150, 1972).

Ammonia can also lead to improper and delayed wound healing. All healing wounds tend to be quite alkaline because of alkalosis which develops from the loss of $CO_2$. The $CO_2$ forms carbonic acid when combined with water and is lost by diffusion from high tissue concentrations to low air concentrations. This alkalosis of surface wounds markedly enhances ammonia intoxication. Ammonia is found as a constituent in 90% of open granulating wounds caused by the action of bacterial urease. (Surg Gynecol & Obs 178:745, 1973).

A manifestation of ammonia toxicity is seen everyday in hospitals that treat patients with impaired liver function such as cirrhosis of the liver. Liver damage can be produced experimentally in animals by the injection of urease into blood which also contains urea. As will be described, the cirrhotics frequently suffer from ammonia intoxication resulting from an increase in free ammonia levels in the blood. The predominant toxic manifestations of high ammonia levels in humans is encephalopathy. The neurological manifestations that accompany this dysfunction of the central nervous system (or encephalon) are so striking that they overshadow the other toxic effects of ammonia. High concentrations of ammonia lead to decreased mentation and mental confusion, symptoms which are not unlike a dementia. Even higher levels of ammonia in the blood stream leads to stupor, coma and eventually, death.

Humans do not form ammonia from urea in the body (Biochem & Biophys Acta 151:646, 1968) and the small amount of ammonia which is formed and circulates in the blood of normal humans is formed in the kidney from glutamine and not by splitting urea. Large quantities of ammonia are formed in the gastrointestinal tract and the highest concentrations of ammonia in the body are found in the portal vein blood coming from that organ. The ammonia is derived by hydrolysis of urea. The harmful effects of this ammonia formed in the colon must be prevented from exerting toxic effects throughout the body's organ systems. Toward this end, the blood from both the small and large intestines is drained by a special set of veins. These veins comprise the portal system. The portal system takes blood directly from the gastrointestinal tract to the liver; only after purification in the liver does the blood enter the general systemic circulation. The large quantity of ammonia formed each day in the gastrointestinal tract is removed by the liver and does not enter the circulating blood in normal people. Intestinal ammonia is mainly produced in the colon. Walser has shown that about 20% of all the urea in the body is converted each day into ammonia in the colon by bacteria. (J Clin Invest 38:1617, 1959). Urea diffuses into the colon from the circulating blood, where it is usually present in concentrations under 20 mg per 100 ml. The urea in the lumen of the large bowel is instantaneously converted to $NH_3$, which is absorbed by the mucosa of the colon into the portal vein which transports it to the liver. In the liver, $NH_3$ combines with citrulline to form arginine. The enzyme arginase hydrolyzes the arginine to urea and ornithine. The latter is transformed to citrulline first by the addition of $CO_2$, and then by $NH_3$ to complete the cycle described by Krebs and Henseleit. In some situations such as kidney disease, dehydration, or hemorrhage in the gastrointestinal tract, the blood urea level is considerably higher. This increases the amount of ammonia which is formed to very toxic levels. In cirrhotics, some portal venous blood bypasses the liver through collateral veins. Also, because of impaired hepatic function, all of the ammonia is not detoxified by the liver and converted to urea. The ammonia then enters the circulating blood and often produces ammonia intoxication. It is not uncommon for cirrhotics to die in coma after a hemorrhage in the GI tract from a ruptured varix. Blood in the GI tract significantly raises the urea concentration in the intestines and blood increases the conversion of urea to ammonia. Also, animals whose portal vein blood is surgically diverted into the systemic circulation develop severe ammonia intoxication when blood is introduced into the stomach. If the small bowel contents are not allowed to reach the colon in such animals, the ammonia intoxication is very mild, showing that it is the bacterial action on the digested blood in the colon that produces the ammonia intoxication. The seriousness of the colonic content in producing ammonia intoxication in cirrhotics has lead some clinicians to advocate excluding the colon from the GI tract by surgical ileostomy. Another approach to limit ammonia intoxication has been the sterilization of the bowel by the administration of antibiotics. (Proc Exp Biol Med 88:130, 1955).

Urea itself is non-toxic and is present in all tissues of the body. Urea is eventually excreted by the kidneys and appears in the urine. Therefore, it can be seen that a healthy body is ideally suited to handle high ammonia loads encountered in the colon and to render the ammonia harmless. This ammonia is eventually excreted in the form of urea thereby eliminating the harmful metabolite from the body.

Ammonia toxicity is encountered frequently in the alcoholic cirrhotic, although hepatic encephalopathy is encountered in other diseases that result in increased ammonia levels in the blood. Cirrhosis is a general term that includes destruction of functional liver cells as well as a fibrosis or scarring of the liver in response to the injury. Since cirrhosis is a disease of the liver and the liver is predominantly responsible for clearing ammonia from the blood, it can be easily seen how a liver disease of this nature would result in toxic levels of ammonia in the circulating blood.

As noted, the ammonia load delivered to the liver is derived from the gastrointestinal tract. Gastrointestinal ammonia is derived from two sources. One source is ammonia containing compounds that are ingested in the diet and degraded to urea and ammonia. Such compounds are mostly in the form of protein, usually animal protein such as meats, but also to a lesser extent by the ingestion of certain ammonium salts. Because blood contains protein in high concentrations, bleeding in the gastrointestinal tract also promotes ammonia formation.

Urea, the product previously described as an inert product of ammonia metabolism by the liver, is passively secreted into the colon along with other juices that enter the colon from the intestine. The water that is secreted and reabsorbed from the colon is part of the overall salt and water turnover in the body. There is an average not absorption of three liters of water per day in the colon: the colon secretes approximately eight liters of water and reabsorbs eleven liters. (Postgrad Med J 41:435, 1965). The delivery of this large secreted volume to the colon brings about substantial diffusion of urea to the colon which is carried along with the water. The urea is a passive part of the fluid that traverses into the colon during this stage; 'passive' means that no energy consuming process secretes urea into the colon but rather that the urea merely accompanies water into the colon. Once in the colon, the urea delivered in this manner is instantaneoulsy converted into ammonia by bacteria present in the colon. As a consequence, urea is never a constituent of colonic contents. (Clin Sci 33:89, 1967).

It has been estimated that 20% of the total body urea is converted to ammonia each day in the colon. Most of the anaerobic bacteria present in the colon contain the enzyme urease, which is capable of splitting urea into its ammonium and carbon dioxide components. This is a process exactly opposite of that accomplished in the liver. It should be noted that all humans have bacteria colonizing the colon and many of these bacteria have urea splitting properties. Urease occurs naturally only in plant life and is not found in human tissues. In the normal person, ammonia created by these micro-organisms is simply reabsorbed in the colon and redirected into the liver by the portal system. In cirrhotic patients, however, these bacteria create an additional ammonia load on the already compromised liver. Indeed, cirrhotics commonly exhibit gastric bleeding which leads to still more colonic ammonia output.

The current state of the art in treating patients with toxic levels of ammonia in their systems is to try to reduce the degree of ammonia production. Patients are placed on low protein diets thereby reducing the amount of ammonia and ammonium compounds delivered to the intestinal system. Lactulose, a sugar not degraded by intestinal enzymes or absorbed in the intestines is not encountered in the diet of humans. This material when ingested reaches the colon where the bacteria of the colon convert it partly to lactic acid. (Gastronenterol 74:544, 1978). This results in a decrease in the pH of the colonic contents further resulting in the conversion of neutral charged ammonia to the positively ionized ammonium ion. Ionized ammonium does not penetrate the cell membrane readily and, therefore, is not absorbed by the intestinal cell in the lumen of the colon. (Am J Surg 119:595, 170). Patients treated for ammonia toxicity are administered large volumes of fluid so as to increase urinary output and large urea excretion by the kidneys.

Sick patients require protein and cannot be put on a diet of zero protein diet content, even though this would decrease the quantity of ammonia derived from protein metabolites. There is an obligate loss of protein every day that must be replenished by ingested foodstuffs. Most of the loss occurs by conversion of protein to urea in the body. Obligate protein loss comes from use of proteins for sources of energy as well as the normal wear and tear of proteins as they perform their daily functions. There are a number of obligate sources of protein loss, not the least of which is loss from the intestinal tract where the mucosa, or the lining of the intestines, is replaced every two to four days in the normal person. As old and worn out cells are sloughed off into the tract, they are replaced by new cells. If the sloughed cells, which are protein rich, come from the beginning of the gastrointestinal tract, they are digested as food and their valuable amino acids are absorbed and recycled. (Anat Record 100:357, 1948). However, cells lost near the end of the tract are past the digestive part of the system and are not broken down into absorbable components. Their protein is lost in stool and must be replaced.

Therefore, it can be seen that the treatment of a cirrhotic suffering from ammonia toxicity requires a delicate titration between a protein need on one hand and the consequences of ammonia toxicity on the other hand. Anything that could sway the balance towards allowing an increased protein intake or more efficient use of a given protein load would be very helpful in treating the cirrhotic patient.

It can also be seen that there is a clear need for methods of decreasing the splitting of urea in the colon to ammonia which is then reabsorbed and taken by the portal system to the liver. This conversion of urea back to ammonia in the colon and then from ammonia back to urea in the liver represents a "futile cycle". This futile cycle wastes the already compromised function of the liver by making it do the same job many times. Preventing the conversion of urea to ammonia in the colon would help decrease the loss of colonic mucosal cells and their protein from the gastrointestinal tract. It has been shown that the ammonia created in the colon reduces the life span of the colonic mucosal cells. These colonic mucosal cells are susceptible to ammonia concentrations. As cells, they are high in protein and their sloughing into the colon accounts for a significant portion of the obligate protein loss from patients and animals. Therefore, by reducing the splitting of urea to ammonia in the colon, two important functions would aide in the treatment of the cirrhotic patient. First, the liver would be spared the chore of driving the futile cycle between ammonia and urea as described above and secondly, the amount of protein that would have to be ingested in the diet to compensate for the obligate protein loss could be reduced. Overall, this would account for a significant decrease in the deliverance of ammonia to the compromised liver and allow the liver to better control ammonia levels. It would also lead to increased use of ingested protein in farm animals reducing the need for protein in the diet.

One way to reduce the amount of ammonia produced in the intestines and returned to the liver would be to disable the urease-carrying bacteria in the colon and thereby stop the aforementioned cycle. Many attempts at this maneuver have been tried in the past using antibiotics. Another method has involved the use of acetohydroxamic acid which is an inhibitor of urease; by inhibiting urease from carrying out its urea splitting function, the liver is spared the extra ammonia load and the damage which ammonia inflicts on the hepatic cells. Unfortunately, acetohydroxamic acid is carcinogenic and toxic and requires continued use. Therefore, it cannot be used therapeutically to decrease ammonia toxicity and it would be costly to continue the drug indefinitely.

Another method attempted by the prior art has been the inducement of an antibody response to urease in patients at high risk for ammonia toxicity. (Am J Med 35:804, 1963).

An antibody is a protein that is synthesized in white blood cells in response to recognition of a foreign particle, or antigen, in the blood. The antibodies created are part of the immune mechanism to foreign molecules in the blood stream and represents the bodys means of defense against invasion with foreign molecules as for instance disease bacteria. This antibody-antigen interaction of the globulin with the antigen inactivates the antigen. An antibody seeks out and binds to the appropriate antigen which results in the loss of activity of the antigen or antigen containing substance/organism until it is eliminated from the system. If the antigen is an enzyme, the antibody neutralizes its enzymatic activity probably by spatially occluding or interacting with the active portion of the enzyme molecule.

Antibodies can inactivate the foreign molecules in the blood stream in a number of different ways. An antibody can bind to and block substrate needed by the organism for survival. It might bind to vital structures on the organism, disrupting function and rendering the organism inviable. Further it can attach to the surface of the foreign particle and induce other defense mechanisms to respond in a manner that would result in the death or destruction of that particle such as in phagocytosis. The antibody reactions are employed in medical immunizations against diseases. A patient is injected with a non-hazardous antigen that will induce the formation of an antibody that will react with the antigen. If this safe antigen is sufficiently similar to a harmful antigen, then the body will prepare the antibody in advance of actually being exposed to the harmful antigen. This is called cross-reactivity of antibodies. Cross-reactivity denotes the ability of certain antibodies, which are highly specific in terms of their ability to recognize the exact foreign particle for which they were created, to react with similar particles that were not identical but sufficiently similar. In this way toxins such as tetanus toxin can be modified to form toxoids which are non toxic but still induce antibody formation with antibodies that will react to the original unmodified toxin. In this manner the body can be induced to mount a primary defense against a toxic substance under controlled non-threatening conditions rather than when later confronted with the actual hazardous disease, and will have the presynthesized antibody already on hand to combat the disease.

A known urease which will induce an antibody which cross-reacts with bacterial urease is the Jack Bean urease, which can be extracted from plants and crystalized for purity. Unfortunately, the urease used for immunization is also metabolically active. It splits urea to ammonia and rapidly induces severe ammonia toxicity, the very condition the immunization is intended to deter. Therefore, immunization with Jack Bean urease requires very small, repeated doses a tedious and dangerous process over a prolonged time period. The treatment has not advanced past the experimental stage due to actual instances of deep coma from ammonis intoxication secondary to the treatment. There is a risk of death due to ammonia toxicity during the immunization period.

Various attempts have been made to modify the Jack Bean urease molecule with the aim of retaining its ability to induce antibody formation against the enzyme while destroying its enzymatic properties. However, all such attempts have failed. Such methods have included iodination, denaturing with heat, oxidation and other chemical treatments. Therefore, there still remains a desperate need for a urease or a urease-like protein similar enough to natural urease so as to cause an antibody response to urease but different enough so as to be metabolically inert and a process for manufacturing of the same.

Another urease antigen has been described as a treatment for ammonia intoxication in cirrhotics, there are many other important usages in medicine. For instance, blood ammonia levels rise in hemorrhagic shock which adversely influences the outcome. (Surgery 34:1, 1953). In patients with kidney disease, the urea nitrogen levels in the blood may reach levels in excess of 10 times the normal value. The excessive formation of ammonia in the colon in this condition can cause a severe type of uremic colitis or severe ammonia intoxication in patients with liver disease. (Dialysis and Renal Transplant 4:245 Ex Med Found, 1968). Immunization in patients with chronic renal failure would prevent this. (Am. J. Surg. 135:53, 1978) Urease has been found to be extremely significant in the production of Pyelonephritis by some ammonia producing organisms. (J Pathol 97:43, 1969). Similarly, some patients are renal stone formers because of chronic infections with urea splitting organisims such as proteus. (Invest Urol 11:228, 1973). The alkaline urine caused by ammonia formation causes a precipitation of urinary calcium with resultant chronic stone formation. It has been demonstrated that animals whose livers are partly extirpated regenerate new liver tissue much faster when the animals are immunized against urease. Also, chronically infected slow healing skin ulcers have been shown to contain large amounts of ammonia produced by urea splitting organisms. (Surg Gyn & Obs 178:745, 1973). This alkalinity of wounds containing ammonia is inappropriate not only because of ammonia toxicity to regenerating cells but also because the pH shift prevents the oxyhemoglobin from releasing its oxygen even at low oxygen tensions. Hence, the alkaline wounds are deprived of an oxygen supply. Since ammonia formation in the colon has been shown to induce early death of the mucosal cells, which is not present in germ free animals which do not form ammonia in the colon, urease immunization may be important in colonic healing. (Am J Surg 135:53, 1978). It should be noted as well that the growth of livestock may be enhanced since protein loss through the stool will be prevented. Also, the unnecessary ammonia to urea cycle within the body is energy consuming and will be eliminated by urease immunization. In addition, some serious infections with proteus vulgaris and other organisms which are strong urease producers can be ameliorated by urease immunization. Although the previous discussion dwells on liver disease, there are a number of situations in veterinary and human medicine where immunization against urease would be of great value. (Agricultural Sci Rev, page 9, Oct. 1970). Urease immunization may increae the growth and efficience of Livestock Food. (J Anim Sc 24:105, 1965; J nutrit 82:93, 1964).

A congenital deficiency in ornithine transcarbamy lase, which is one of the enzymes in the Krebs urea cycle can cause death in newborns from hyperammonia. Such deaths could be prevented by immediate passive immunization with urease antibodies which could be prepared from immunized donors or by the monoclonal tissues culture technique.

SUMMARY OF THE INVENTION

The present invention comprises a non-enzymatic urease antigen which induces the formation of antibodies in humans, which antibodies are cross-reactive to urease produced by colonic bacteria. The invention further comprises a method for production of a covalently bonded non-enzymatic urease antigen composition, and a method for the use thereof. The material composition of the present invention successfully avoids the active induction of ammonia intoxication which has been the hallmark characteristic of the prior art. The material composition is characterized by urease molecules which are covalently bonded to gluteraldehyde to produce molecules with a molecular weight in the range from 250,000 to 1,000,000.

DETAILED DESCRIPTION OF THE INVENTION

The present invention utilizes an active urease antigen such as Jack Bean or bacterial urease, which is chemically combined with glutaraldehyde. The method for treatment utilizing the material composition of the present invention involves innoculation with the material composition. In test animals, it has been found that the material composition of the present invention is parenterally non-toxic in quantities representing a dosage increase factor of 100,000 over that known in the prior art with unmodified purified natural urease. The period of immunization and the effectiveness of the immunization with glutaraldehyde modified enzyme favorably influences the course in liver disease.

Moreover, it has been found that the material composition of the present invention offers a long shelf life in lyophilized powder form at room temperature. Thus, the material is available for treatment of patients without the need for expensive storage systems.

The best mode and preferred embodiment of the present invention is set forth in the following detailed description thereof, taken in conjunction with the accompanying examples.

According to the method of the present invention, an active urease, such as crystalline Jack Bean urease, is diluted and a solution of glutaraldehyde is prepared. The urease solution and the glutaraldehyde solution are then mixed, and a reaction ensues. In the reaction, urease molecules are covalently bonded to glutaraldehyde molecules, producing a molecule with a molecular weight in the range from 250,000 to 2,000,000. When the reaction has been completed, the excess glutaraldehyde is neutralized and the resulting solution is subjected to lyophilization after being dialyzed. The resulting powder may be stored at room temperature over an extended period.

The method of treatment of the present invention comprises preparation of an injectable dosage by dissolving an appropriate quantity of the powder material in a sterile non-toxic solution, and injecting the dosage into the subcutaneous tissue or muscular tissue of the patient. The material itself is non-toxic and has been shown by vitro tests and animal tests to be totally non-enzymatic, therefore avoiding the ammonia intoxication characterizing the prior art. Thus, dosages can be increased by a factor of 100,000 over those known in the prior art. Subsequent testing of the animals showed that injections of active urease were neutralized, as were the effects of ureaseproducing bacteria injected into various bacteria.

The following examples are offered to further explain and exemplify the present invention:

EXAMPLE 1

While bacterial urease can be used, the readily available Jack Bean urease has proven satisfactory. Commercially available crystaline Jack Bean urease is dissolved in water or saline solution to give a concentration equivalent to 50 Sumner units per milliliter. Sumner units are an expression of the activity of the urease and are determined as described below in Example 2.

To the solution containing 50 Sumner units of urease, glutaraldehyde is added to give a final concentration of 0.01% (W/V) glutaraldehyde. The reaction mixture is kept at 37 degrees centigrade for a period not greater than 48 hours. The interval of 48 hours has been previously determined by testing the enzymatic activity of the reaction mixture during the course of the reaction. At this time, approximately 95% of the urease is found to be inactivated. The reaction is allowed to proceed until all of the urease activity has been neutralized in the mixture. This may require an additional three to six hours. The reaction is then stopped by the addition of sodium bisulfite to neutralize unreacted glutaraldehyde or simply by dialyzing the reaction mixtue. Following dialysis, the material is lyophilized and the powder put aside for storage and antibody testing. No enzymatic activity is present in the lyophilized powder which is suspended in saline solution prior to immunization.

EXAMPLE 2

A Sumner unit determination is carried out as follows:

A substrate is prepared from $1\frac{1}{2}$ grams of urea and 25 milligrams of crystaline bovine serum albumin in 50 milliliters in 0.75 phosphate buffered to pH 7. A known sample of urease enzyme with 0.02 Molar $PO_4$ Buffer at pH 7 to 1.0 milliliter.

The procedure utilizing the above reagents is carried out immediately as follows: With reagents at room temperature (approximately 20 degrees centigrade) two drops of Bromcresal Green-Methyl Green Kjeldahl indicator are added to one milliliter of substrate and one milliliter of 0.02 Molar Buffer and the enzyme solution titrated with 0.1 Normal HCl to first purple endpoint. The milliliter of 0.1 Normal Hydrochloric Acid needed to reach the endpoint is recorded as (A).

To assay an unknown concentration of enzyme placed on one milliliter of substrate, 2 drops of indicator is added to one milliliter diluted enzyme at 0 time which is allowed to stand for exactly five minutes at room temperature. (20 degrees centigrade). After 5 minutes, 0.1 Normal HCl is added to reach the original endpoint and the titration is continued beyond to the first purple color. The total milliliters of the 0.1 Normal HCl needed to reach the endpoint (B) are recorded. A calculation is carried out using the formula (B-A$\times$0.10$\times$14= the numbers of Sumner units of urease per milliliter in the solution to be assayed.

EXAMPLE 3

Rabbits and mice were injected with the lyophilized material from Example 1 and were bled at the end of one week and after a second injection at the end of two weeks for determination of antienzyme in the circulating blood. Titres of greater than 100,000 were usually achieved with a tanned, red cell agglutination test. The serum was tested against unmodified, purified urease. All showed good antibody arcs on an Ouchterlony plate when an unmodified crystalline urease enzyme was placed in the trough. This test indicates that the modified urease antigen is capable of producing antibodies in the immunized animal which will neutralize purified, unmodified urease. The serum of the animals when added to urease in solution and mixed with urea inhibits ammonia formation. The lethal dose urease which killed 99% of the animals (LD99) was 60 to 70 Sumner units per kilogram of body weight in nonimmunized rats. However, the LD99 for urease immunized rats was more than 10 times greater. More than 750 Sumner units per kilogram weight was required.

Additionally, humans were immunized with 10 milligrams of the inactive complex in weekly injections over a period of two weeks or three weeks. Good enzymes titres were found in patients at the end of fourteen days. Isotope studies injecting $C_{14}$ labeled urea into immunized humans disclosed that internal urea turnover (in the large bowel) was completely prevented. All of the labelled urea was excretion in the urine in contrast to normal humans who cleave some of the radioactive compound and expire $C_{14}$ labelled $CO_2$. No untoward systematic response was encountered and there was no undue inflammatory response at the injection site.

Purified, crystalized urease is a protein of the globulin type. The molecular weight of the native material is approximately four hundred eighty thousand with an isoelectric point at a pH of 5.0 to 5.1. The glutaraldehyde modified urease has an average molecular weight of approximately two million.

While general embodiments of the present invention has been described, it will be apparent to those of ordinary skill in the arts that various alternative configurations and embodiments can readily be adapted to the present invention and are considered to fall within the scope thereof as set forth in the following claims.

What is claimed is:

1. A non-enzymatic antigen which is the reaction product of urease and glutaraldehyde to form a covalently bonded molecule having an average molecular weight of about 250,000 to two million.

2. The antigen of claim 1 wherein said urease is Jack Bean urease.

3. The antigen of claim 1 wherein said urease is bacterial urease.

4. The antigen of claim 1 which induces antibody formation in animals which is cross-reactive to urease.

5. A method for inhibiting ammonia toxicity in animals which comprise administering to said animals a therapeutically effective amount of the reaction product of urease and glutaraldehyde which forms a covalently bonded molecule having an average molecular weight ranging from about 250,000 to two million.

6. The method of claim 5 wherein said animals are humans.

7. The method of claim 5 wherein said urease is Jack Bean urease.

8. The method of claim 5 wherein said urease is crystalized.

9. The method of claim 5 wherein said urease has an isoelectric at a pH ranging from 5.0 to 5.1.

10. The method of claim 5 wherein said urease is dissolved in fluid to give a concentration equivalent to 50 Sumner units per milliliter.

11. The method of claim 5 wherein said reaction product is a non-enzymatic antigen having the ability to induce cross-reactive antibody formation.

12. A method for making an active urease antigen which is chemically combined with glutaraldehyde comprising the steps of:
   (a) dissolving the urease antigen in a fluid to form a solution having a concentration of previously prepared Sumner units per milliliter;
   (b) adding glutaraldehyde to the solution of form a reaction mixture having a concentration of 0.01% glutaraldehyde;
   (c) holding the reaction mixture for a period ranging from 48 to 54 hours; and
   (d) lyophilizing the reaction mixture.

13. A method claimed in claim 12 wherein said fluid solution is water.

14. A method as claimed in claim 12 wherein said fluid solution is a saline solution.

15. A method as claimed in claim 12 wherein said reaction mixture is kept at about 37 degrees centigrade during the holding period.

16. A method as claimed in claim 12 comprising an additional step after step (c) comprising adding sodium bisulfite to neutralize unreacted glutaraldehyde.

17. A method as claimed in claim 12 wherein the glutaraldehyde modified urease has an average molecular weight of about two million.

* * * * *